United States Patent [19]

Dutton et al.

[11] 4,049,525
[45] Sept. 20, 1977

[54] CORROSION TEST CELL

[75] Inventors: Daniel Ronan Dutton, Woodhaven; Thomas Carl Musolf, Southgate, both of Mich.

[73] Assignee: BASF Wyandotte Corporation, Wyandotte, Mich.

[21] Appl. No.: 732,540

[22] Filed: Oct. 14, 1976

[51] Int. Cl.² ............................................. G01N 27/46
[52] U.S. Cl. ................................................ 204/195 C
[58] Field of Search ............................. 204/1 C, 195 C; 23/230 C, 253 C; 324/29

[56] References Cited
PUBLICATIONS

D. A. Carter et al., "A Polarization Study of Cooling Water Corrosion Inhibitors," *Materials Protection*, Nov. 1969, pp. 61–66.
ASTM Standard G5–72, "Standard Reference Method for Making Potentio Static & Potentiodynamic Anodic Polarization Measurements" (1972).
B. E. Wilde, "An Assembly for Electrochemical Corrosion Studies. . .," *Corrosion*, Nov. 1967, pp. 331–334.
Product Literature, Corrosion Cell Kit–Model 9700, Princeton Applied Research Corp., Copyright 1975.
R. E. Geisert et al., "A Versatile Polarization Cell System," *Corrosion*, vol. 32, Oct. 1976, pp. 407–410.

*Primary Examiner*—John H. Mack
*Assistant Examiner*—Aaron Weisstuch
*Attorney, Agent, or Firm*—Norbert M. Lisicki; Bernhard R. Swick; Robert E. Dunn

[57] ABSTRACT

A corrosion test cell suitable for determining the electrochemical corrosion parameters of metals in corrosive liquid environments. The cell comprises an electrically non-conductive vessel with a plurality of metallic rods connectable to test electrodes, which electrodes extend into the liquid environment contained therein.

4 Claims, 4 Drawing Figures

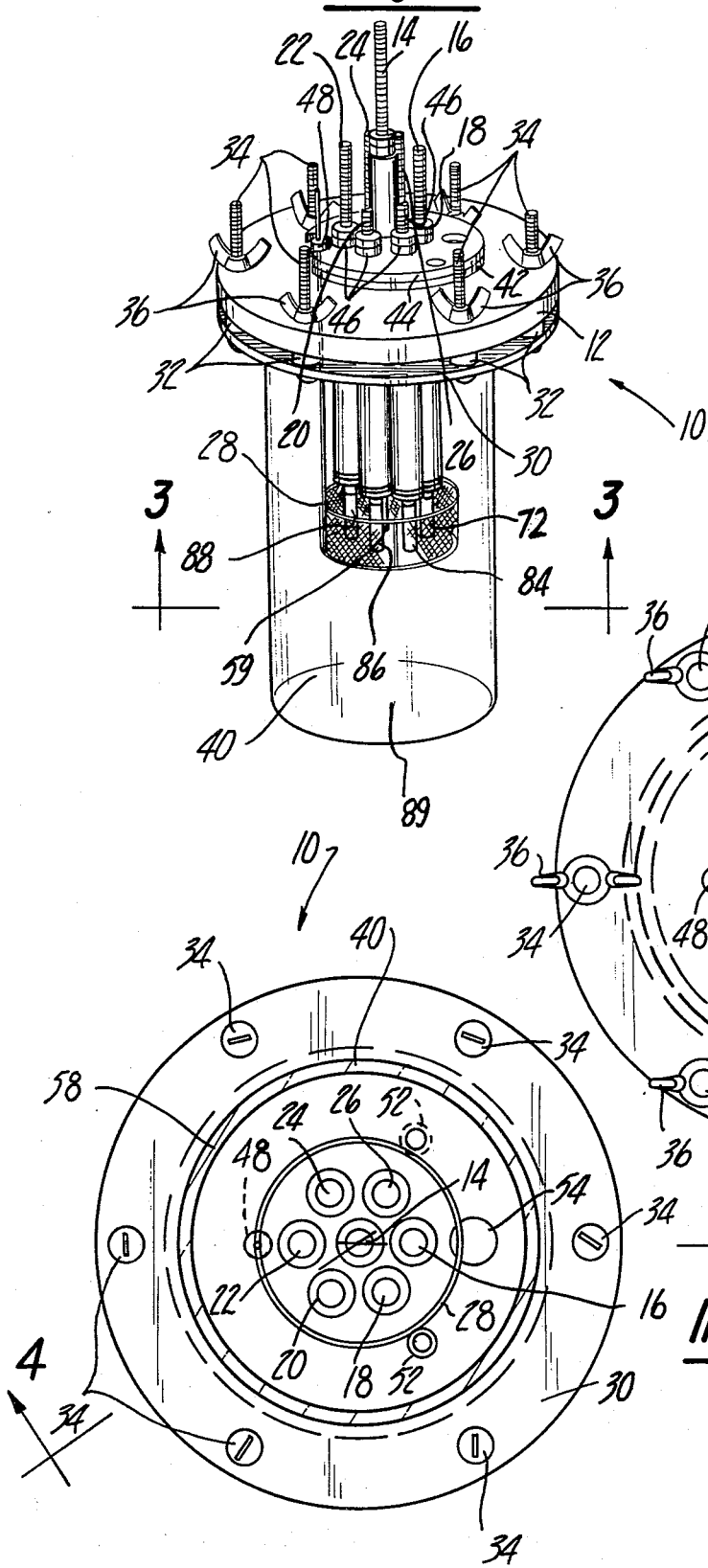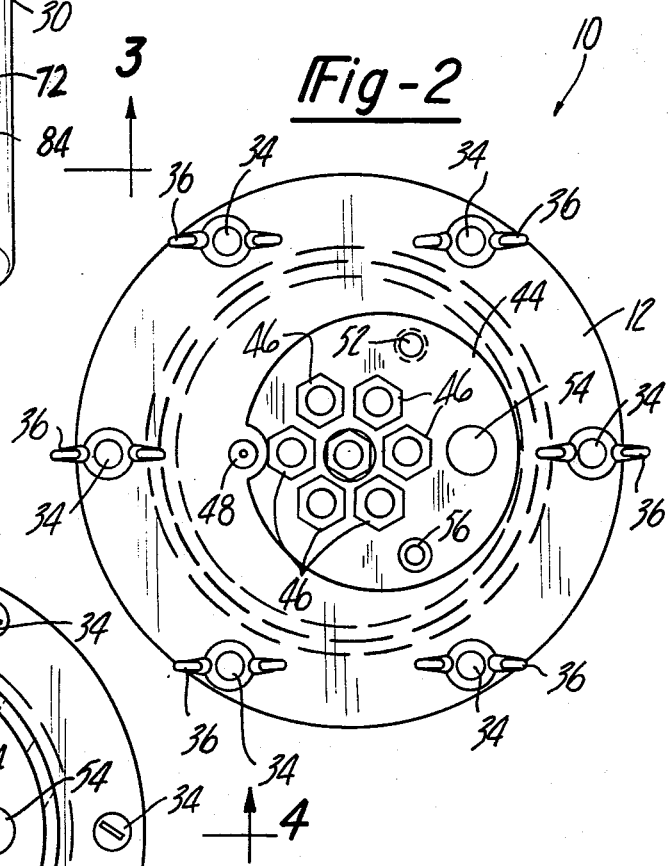

CORROSION TEST CELL

BACKGROUND OF THE INVENTION

1. Field of the Invention

This invention relates to the design and use of corrosion test cells useful in determining electrochemical corrosion parameters of metals in corrosive liquid environments.

2. Description of the Prior Art

In the evaluation of aqueous liquids which are employed as hydraulic fluids or as heat exchange liquids it is extremely important to know the rate at which various metals corrode within that liquid environment. This enables the formulator of the liquids to select effective corrosion inhibitors for inclusion in these fluids. Corrosion test cells for laboratory use in determining the electrochemical corrosion parameters of metals in corrosive environments have been described by Stern, M., *J. Electrochem. Soc.*, 102, 609 (1955), and Greene, N. D., "Experimental Electrode Kinetics", Rensselaer Polytechnic Institute, Troy, N. Y. 1965, with modifications relating to the mounting of test metal electrodes described by Stern, M., Makrides, A. C., *J. Electrochem. Soc.* 107 (1960) and Agrawal, A. K., Damin, D. C., McCright, R. D., and Staehl, R. W., *Corrosion*, 31, 262 (1975). Furthermore, a number of review articles on the subject have appeared, specifically, Wilde, B. E., "Some Considerations in the Design of Electrodes for Electrochemical Studies at High Temperature and Pressure", presented at the International Conference on High Temperature, High Pressure, Electrochemistry in Aqueous Solutions, University of Surrey, England, January 1973 and Damin, D. G., "Electrochemical Studies of Several Iron-Nickel-Chromium Alloys in Dilute Aqueous Solutions at Temperatures Up to 250° C.", M.S. Thesis, The Ohio State University (1974). The test cell described by Greene is widely used in laboratories for electrochemical examination of corrosion and is generally referred to as the "Greene Cell". It is described in ASTM G5-72. None of the above disclose the design of the claimed corrosion test cell assembly.

SUMMARY OF THE INVENTION

In accordance with this invention there is provided a corrosion test cell suitable for determining the electrochemical corrosion parameters of metals in corrosive liquid environments. An electrically non-conductive vessel is provided for receiving the electrolyte solution covered by an electrically non-conductive cover member. A plurality of electrical conductors are supported in the non-conductive cover member in electrical isolation and extend axially from both ends thereof, wherein one exposed end of each conductor forms a terminal to receive a metallic electrode which is placed into said electrolyte solution and the other exposed end of each of said conductors is connected to a suitable electrical conductor. Insulating fluid seals encircle the terminals and provide for fluid tightness between the terminals and the electrodes which are employed. An electrical source provides circuits with the electrodes for the determination of the electrochemical corrosion parameters.

BRIEF DESCRIPTION OF THE DRAWINGS

FIG. 1 is a perspective view of the corrosion test cell assembly indicating the location of the various electrode members.

FIG. 2 represents the top view of the base plate employed in the corrosion test cell assembly.

FIG. 3 represents the bottom view of the same base plate taken along the transverse plane 3—3 of FIG. 1.

DESCRIPTION OF THE PREFERRED EMBODIMENTS

Figure 4:
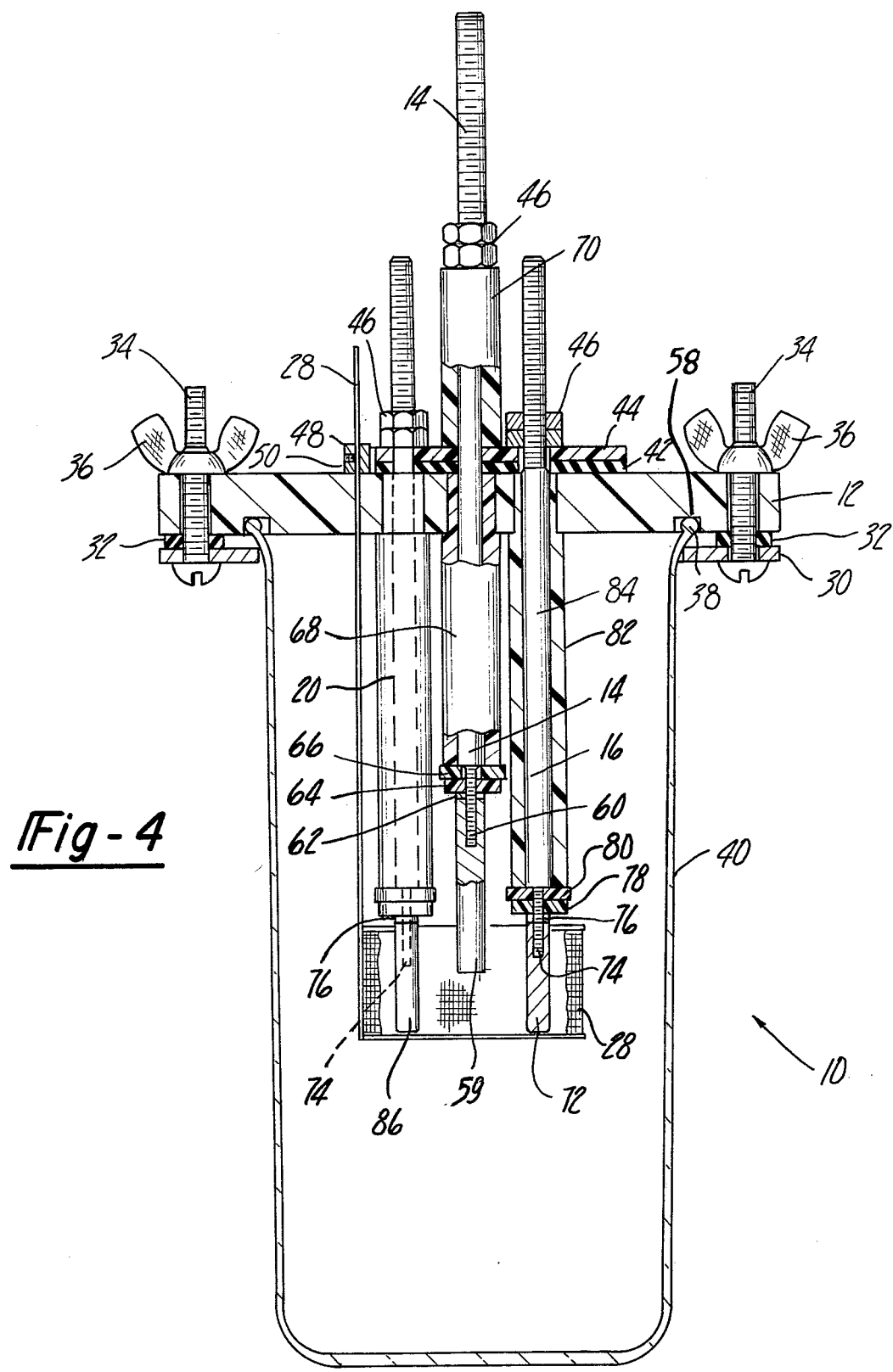
FIG. 4 represents a vertical section of the corrosion test cell assembly of this invention taken along the line 4—4 of FIG. 3.

In FIG. 1 there is illustrated one embodiment of corrosion test cell assembly 10 which can be employed for determining the electrochemical corrosion parameters of metals in various corrosive environments. Corrosion test cell assembly 10 is composed of cover member 12 which holds seven metallic rods 14, 16, 18, 20, 22, 24 and 26 in electrical isolation and extending axially from both ends thereof. One exposed end of each rod forms a terminal connectable to one of the electrodes 59, 72, 84, 86, and 88 and two others (not shown) which are supported in an electrolyte solution 89. The other exposed end of each rod is connected by suitable means to a suitable electrical conductor (not shown) which may lead to a means (not shown) suitable for obtaining the desired potentiodynamic anodic polarization curve, i.e., employed as a potentiostat, an electrometer, a potentiometer, a milliameter, a recorder, a log converter, etc. One electronic unit which incorporates these features in a single unit is the Petrolite ® Potentiodyne analyzer manufactured by the Petrolite Corp., Houston, Tex. Rod 14 is centrally located in cover member 12 and is employed as the support for the reference electrode 59. Rods 16, 18, 20, 22, 24 and 26 are arranged symmetrically around rod 14 and are employed as supports for various test metal electrodes such as 72, 84, 86 and 88. Auxiliary electrode 28 constructed of platinum wire mesh surrounds rods 14, 16, 18, 20, 22, 24 and 26 in such a fashion that a symmetry of current lines exists between the reference electrode mounted on rod 14, auxiliary electrode 28 and any of the test metal electrodes mounted on rods 16, 18, 20, 22, 24 and 26. Cover member 12 is connected to a clamping collar 30 separated by a plurality of spacer washers 32 employing a plurality of both machine screws 34 and wing nuts 36. The connection of cover member 12 with clamping collar 30 permits a tight seal over lip 38, shown in FIG. 4, of a vessel 40. The rods 14, 16, 18, 20, 22, 24 and 26 are held on cover member 12 by means of a rubber gasket 42, a polytetrafluoroethylene gasket 44 and a plurality of hexagonal nuts 46. The rod for electrode 28 is held on cover member 12 by means of screen support 48 and set screw 50. (FIG. 4).

FIG. 2 represents the top view of cover member 12 incorporating holes 52, 54 and 56 which may be employed for the insertion of thermometers, condensers, gas inlet tubes, etc.

FIG. 3 represents the bottom view of cover member 12 displaying groove 58 which fits over lip 38 of vessel 40.

FIG. 4 is a cross-sectional view of corrosion test cell assembly 10. Electrode 59 is joined to stainless steel center rod 14 by means of threads 60 employing a small polytetrafluoroethylene thrust washer 62, a large polytetrafluoroethylene thrust washer 64 and a rubber seal washer 66 as a sealing means between electrode 59 and a polytetrafluoroethylene rod sleeve 68. Small thrust washer 62 has the same O.D. as the O.D. of the electrode. The upper portion of rod 14 passes through cover member 12. Polytetrafluoroethylene rod sleeve 70 covers the portion of rod 14 extending through cover member 12, gasket 42 and gasket 44. Rod sleeve 70 is held securely in place by means of hexagonal nuts 46. A sufficient amount of rod 14 extends beyond rod upper sleeve 70 to provide for an electrical connection to a suitable conductor (not shown) for obtaining the polarization curve. Electrode 72 is connected to stainless steel rod 16 by means of threads 74 employing a small polytetrafluoroethylene thrust washer 76, a large polytetrafluoroethylene thrust washer 78 and a rubber seal washer 80 as a sealing means between electrode 72 and a polytetrafluoroethylene rod sleeve 82. The upper portion of sleeve 82 passes through cover member 12. Rod 16 is held securely in place by means of hexagonal nuts 46 screwed down securely against gasket 44. Electrodes such as 84, 86, 88, and two others (not shown) attached to rods 18, 20, 22, 24 and 26, respectively, are constructed and mounted in a manner similar to that of electrode 72 attached to rod 16.

Vessel 40 may be constructed of any electrically non-conductive material such as glass, polyethylene, polypropylene, polytrifluorochloroethylene and polytetrafluoroethylene, preferably glass.

Cover member 12 may be constructed of such electrically non-conductive materials as polytetrafluoroethylene, polytrifluorochloroethylene, polyethylene and polypropylene, preferably polytetrafluoroethylene.

The rod sleeves and the thrust washers may also be constructed of any electrically non-conductive materials such as polytetrafluoroethylene, polytrifluorochloroethylene, polyethylene and polypropylene, preferably polytetrafluoroethylene.

The corrosion test cell which is the subject of this invention has many advantages which improve upon the conventional Greene Cell. It is quite versatile since as many as six test electrodes may be tested under identical conditions. It is inexpensive; it is constructed of readily available materials; it is durable, being constructed primarily of polytetrafluoroethylene and stainless steel; the test cell as claimed in the application can be used to examine the electrochemical corrosion parameters of six test metal specimens in the same test corrodant fluid simultaneously; and the amount of corrodant fluid to be studied is only limited by the volume of the vessel to which the electrode cover member is attached.

When using a glass vessel to contain the corrodant liquid the test cell claimed herein can be used to determine the electrochemical parameters of metal test specimens in any media with the exception of concentrated caustic or hydrofluoric acids and can be employed over a temperature range of from below 0° C. to above 200° C. without undue difficulty. The atmosphere in the test cell can be controlled by insertion of the proper equipment as provided for in the cell. The use of stainless steel rods encased by polytetrafluoroethylene tubing eliminates any breakage when mounting electrodes. Since the corrosion test cell of the present invention can be used to monitor the electrochemical parameters of up to six test electrodes it can also be used to monitor the electrochemical parameters of metals which are galvanically coupled and in the same test corroding liquid.

The test electrodes which are employed in the corrosion test cell are formed of those metals which it is desired to determine their electrochemical corrosion parameters. Such materials may be iron, steel, aluminum, brass, copper, nickel, lead, titanium, chromium and alloys thereof.

The reference electrode may be suitable reference electrode, however, it is preferable to use a silver, silver chloride reference electrode.

The test cell is assembled in such a manner that the reference electrode is located in the center. The electrode is attached to the stainless steel rod in such a manner as to provide a leakproof compression of seal washer, outer rod sleeve, small thrust washer, and large thrust washer. The six test metal electrodes are mounted symmetrically about the center reference electrode and are attached in such a manner as to provide a leakproof compression of the various washers. It is obviously essential for proper electrochemical measurements that none of the stainless steel rods are exposed to the corrodant fluid. Symmetrically spaced around the test electrodes is an auxiliary electrode constructed of a noble metal such as platinum or gold. Provisions are made in the cover member for the inclusion of thermometer, condenser and gas diffusion tube. These and the stainless steel rods are tightly sealed against the cover member by means of a compressible gasket fixed between base plate and support rod mounting plate. The compressible gasket is preferably constructed of silicone rubber.

It will be obvious from the foregoing that various modifications of what has been specifically described may be utilized without departing from the invention as defined in the following claims.

The embodiments of the invention in which an exclusive property or privilege is claimed are defined as follows:

1. A corrosion test cell assembly suitable for determining the electrochemical corrosion parameters of metals in corrosive liquid environments comprising;
   a. an electrically non-conductive vessel for receiving an electrolyte solution,
   b. an electrically non-conductive cover member adapted to be secured to said vessel,
   c. a plurality of metallic rods supported in said cover member in electrical isolation, both ends of said rods extending axially from said cover member, one end of each rod having terminal connector means thereon and supported within said vessel, the other end of each of said rods being connectable to suitable electrical conducting means, one of said rods being centrally located in said cover member, the remaining rods being arranged symmetrically around said central rod,
   d. a reference electrode secured to said terminal means of said centrally located rod and adapted to be supported within an electrolyte solution in said vessel,
   e. at least one of said terminal means of one of the remaining rods adapted to secure a test electrode thereon and supportable within an electrolyte solution in said vessel,
   f. an auxiliary electrode surrounding said reference electrode and said metal rods,
   g. insulating fluid seals encircling said terminal means and adapted to be engaged in fluid tight relationship between said terminal means and electrodes secured thereon, h. said electrical conducting means providing circuits with said electrodes during said determination of electrochemical corrosion parameters.

2. The test cell assembly of claim 1 wherein said cover member is constructed of polytetrafluoroethylene.

3. The test cell assembly of claim 1 wherein said reference electrode is silver, silver chloride.

4. The test cell assembly of claim 1 wherein said auxiliary electrode is platinum wire mesh.

* * * * *